United States Patent
Fabry et al.

[11] Patent Number: 6,013,616
[45] Date of Patent: Jan. 11, 2000

[54] MILD DETERGENT MIXTURES

[75] Inventors: Bernd Fabry, Korschenbroich; Ansgar Behler, Bottrop, both of Germany

[73] Assignee: Henkel Kommanditgesellschaft auf Aktien, Duesseldorf, Germany

[21] Appl. No.: 08/809,283

[22] PCT Filed: Sep. 1, 1995

[86] PCT No.: PCT/EP95/03436

§ 371 Date: Mar. 10, 1997

§ 102(e) Date: Mar. 10, 1997

[87] PCT Pub. No.: WO96/08549

PCT Pub. Date: Mar. 21, 1996

[30] Foreign Application Priority Data

Sep. 12, 1994 [DE] Germany ............... 44 32 366

[51] Int. Cl.$^7$ ............... C11D 1/16; C11D 1/37; A61K 7/50

[52] U.S. Cl. ............... 510/472; 510/127; 510/130; 510/135; 510/155; 510/490; 510/494; 510/495

[58] Field of Search ............... 510/127, 130, 510/135, 155, 490, 494, 495, 472

[56] References Cited

U.S. PATENT DOCUMENTS

| | | | |
|---|---|---|---|
| 3,086,943 | 4/1963 | Lang | 252/152 |
| 3,226,330 | 12/1965 | Austett | 252/117 |
| 3,291,744 | 12/1966 | Bohrer | 252/161 |
| 4,536,338 | 8/1985 | Urban et al. | 260/400 |
| 4,867,899 | 9/1989 | Ahmed et al. | 252/121 |
| 5,312,932 | 5/1994 | Behler et al. | 554/90 |
| 5,322,957 | 6/1994 | Fabry et al. | 558/23 |

FOREIGN PATENT DOCUMENTS

| | | |
|---|---|---|
| 622 463 | 12/1962 | Belgium . |
| 611 972 | 1/1961 | Canada . |
| 0 256 656 | 2/1988 | European Pat. Off. . |
| 0 318 729 | 6/1989 | European Pat. Off. . |
| 0 559 375 | 9/1993 | European Pat. Off. . |
| 1 208 750 | 2/1960 | France . |
| 1 272 254 | 1/1962 | France . |
| 43 00 325 | 7/1994 | Germany . |
| 941 807 | 11/1963 | United Kingdom . |
| 954 046 | 4/1964 | United Kingdom . |
| 92/09569 | 6/1992 | WIPO . |
| 92/09570 | 6/1992 | WIPO . |
| WO95/23582 | 9/1995 | WIPO . |

OTHER PUBLICATIONS

J. Am. Oil. Chem. Soc. 37, (1960) p. 171.
J. Oil Technol. Ass. Ind. (1972) p. 41.
Indian J. Pharm. Sci. 41, (1979) p. 181.
HAPPI, Sep., (1984) p. 56.
J. Am. Oil. Chem. Soc. 48, (1971) p. 657.
Cosm. Toil, 108, (1993) p. 81.
Tens. Surf. Det., 30 (1993) p. 315.
Surfactants in Consumer Products, J Falbe (ed.), Springer–Verlag, Berlin, 1987, pp. 54 to 124.
Katalysatoren, Tenside und Mineralöladditive, Thieme Verlag, Stuttgart, 1978 pp. 123 to 217.
"Kosmetische Färbemittel" der Farbstoffkommission der Deutschen Forschungsgemeinschaft, published by Verlag Chemie, Weinheim, 1984, pp. 81 to 106.

*Primary Examiner*—Jerry D. Johnson
*Attorney, Agent, or Firm*—Ernest G. Szoke; Wayne C. Jaeschke; Real J. Grandmaison

[57] ABSTRACT

Surfactant mixtures which provide improve dermal compatibility and foam stability contain (a) monoglyceride(ether)sulfates, and
(b) fatty acid condensation products selected from
   (b1) fatty acid isethionates,
   (b2) fatty acid taurates, and
   (b3) fatty acid sarcosinates.

18 Claims, No Drawings

MILD DETERGENT MIXTURES

BACKGROUND OF THE INVENTION

1. Field of the Invention

This invention relates to detergent mixtures with improved dermal compatibility which contain monoglyceride(ether)sulfates and selected fatty acid condensation products, to surface-active formulations containing these mixtures and to the use of the mixtures for the production of surface-active formulations.

2. Discussion of Related Art

Formally, monoglyceride sulfates are products of the addition of sulfur trioxide to the primary hydroxyl group of a glycerol monofatty acid ester. Technically, however, they are complex anionic surfactant mixtures which are normally obtained by simultaneous transesterification and sulfation of mixtures of triglycerides and glycerol and subsequent neutralization.

Monoglyceride sulfates are distinguished by satisfactory performance properties and good dermatological compatibility. Reviews of the production and properties of monoglyceride sulfates have been published, for example, by A. K. Biswas et al. in J. Am. Oil. Chem. Soc. 3,7 171 (1960), by R. Chamanial et al. in J. Oil. Technol. Ass. Ind. 41 (1972) and by J. K. Jain in Indian J. Pharm. Si. 41, 181 (1979).

For many applications, the foaming power, particularly in hard water, and the dermal compatibility of monoglyceride sulfates and the corresponding ether sulfates are not entirely satisfactory.

Accordingly, the problem addressed by the present invention was to find a way of significantly improving the performance and skin compatibility of monoglyceride(ether) sulfates.

DESCRIPTION OF THE INVENTION

The present invention relates to mild detergent mixtures containing (a) monoglyceride(ether)sulfates and
(b) fatty acid condensation products selected from the group consisting of
  (b1) fatty acid isethionates,
  (b2) fatty acid taurates and/or
  (b3) fatty acid sarcosinates.

It has surprisingly been found that mixtures of monoglyceride sulfates or monoglyceride ether sulfates and the fatty acid condensation products mentioned lead to a synergistic improvement in dermal compatibility and to increased foaming power.

Monoglycerides and Monoglyceride Ether Sulfates

Monoglyceride sulfates and monoglyceride ether sulfates are known anionic surfactants which may be obtained by the relevant methods of preparative organic chemistry. They are normally produced from triglycerides which are transesterified to the monoglycerides, optionally after ethoxylation, and subsequently sulfated and neutralized. The partial glycerides may also be reacted with suitable sulfating agents, preferably gaseous sulfur trioxide or chlorosulfonic acid [cf. WO 92/09569, WO 92/09570, Henkel]. If desired, the neutralized substances may be subjected to ultrafiltration to reduce their electrolyte content to the required level.

The monoglyceride(ether) sulfates to be used in accordance with the invention correspond to formula (I):

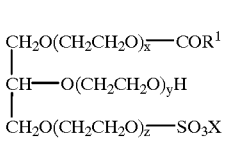

in which $R^1CO$ is a linear or branched acyl group containing 6 to 22 carbon atoms, x, y and z together represent 0 or numbers of 1 to 30 and X is an alkali metal or alkaline earth metal.

Typical examples of monoglyceride(ether)sulfates suitable for use in accordance with the invention are the reaction products of lauric acid monoglyceride, coconut fatty acid monoglyceride, palmitic acid monoglyceride, stearic acid monoglyceride, oleic acid monoglyceride and tallow fatty acid monoglyceride and their ethylene oxide adducts with sulfur trioxide or chlorosulfonic acid in the form of their sodium salts. Monoglyceride sulfates corresponding to formula (I), in which $R^1CO$ is a linear acyl group containing 8 to 18 carbon atoms, are preferably used.

Fatty Acid Isethionates

Fatty acid isethionates are known anionic surfactants which may be obtained by the relevant methods of preparative organic chemistry. They are normally produced from fatty acids which are esterified with isethionic acid in the presence of alkaline catalysts [cf. U.S. Pat. No. 4,536,338 (Unilever)]. A review of fatty acid isethionates was published by R. Login in HAPPI, September, 56 (1984).

The fatty acid isethionates correspond to formula (II):

in which $R^2CO$ is an aliphatic, linear or branched, saturated or unsaturated acyl group containing 6 to 22 carbon atoms and X is an alkali metal and/or alkaline earth metal, ammonium, alkylammonium, alkanolammonium or glucammonium.

Typical examples are fatty acid isethionates derived from caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

Fatty acid isethionates are preferably used in the form of their sodium and/or ammonium salts derived from fatty acids containing 12 to 18 and, more particularly, 12 to 14 carbon atoms. The use of coconut fatty acid isethionate in the form of its sodium or ammonium salt is particularly preferred.

Fatty Acid Taurates

Fatty acid taurates are known anionic surfactants which may be obtained by the relevant methods of preparative organic chemistry. They are normally produced from fatty acids which are condensed with N-methyl taurine in the presence of alkaline catalysts. An overview of this subject was published by R. Bistline et al. in J. Am. Oil. Chem. Soc. 48, 657 (1971) and by K. Miyazawa et al. in Cosm. Toil. 108, 81 (1993).

The fatty acid taurates correspond to formula (III):

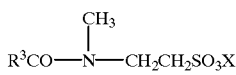

(III)

in which $R^3CO$ is an aliphatic, linear or branched, saturated or unsaturated acyl group containing 6 to 22 carbon atoms and X is an alkali metal and/or alkaline earth metal, ammonium, alkylammonium, alkanolammonium or glucammonium.

Typical examples are fatty acid taurates derived from caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

Fatty acid taurates are preferably used in the form of their sodium and/or ammonium salts derived from fatty acids containing 12 to 18 and, more particularly, 12 to 14 carbon atoms. The use of coconut fatty acid taurate in the form of its sodium or ammonium salt is particularly preferred.

Fatty Acid Sarcosinates

Fatty acid sarcosinates are known anionic surfactants which may be obtained by the relevant methods of preparative organic chemistry. They are normally produced from fatty acids which are condensed with sarcosine (N-methyl glycine) in the presence of alkaline catalysts. A review of fatty acid sarcosinates was published by A. Desai et al. in Tens. Surf. Det. 30, 315 (1993).

The fatty acid sarcosinates correspond to formula (IV):

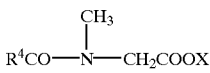

(IV)

in which $R^4CO$ is an aliphatic, linear or branched, saturated or unsaturated acyl group containing 6 to 22 carbon atoms and X is an alkali metal and/or alkaline earth metal, ammonium, alkylammonium, alkanolammonium or glucammonium.

Typical examples are fatty acid sarcosinates derived from caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

Fatty acid sarcosinates are preferably used in the form of their sodium and/or ammonium salts derived from fatty acids containing 12 to 18 and, more particularly, 12 to 14 carbon atoms. The use of coconut fatty acid sarcosinate in the form of its sodium or ammonium salt is particularly preferred.

The detergent mixtures according to the invention may contain the monoglyceride(ether)sulfates and the selected fatty acid condensation products in a ratio by weight of 99:1 to 1:99. With a particularly low irritation potential in mind, a ratio by weight of 50:50 to 80:20 has proved to be advantageous.

Surfactants

The detergent mixtures according to the invention may contain other anionic, nonionic, cationic and/or amphoteric surfactants.

Typical examples of anionic surfactants are alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, fatty acid amide(ether)sulfates, mono- and dialkyl sulfosuccinates, mono- and dialkyl sulfosuccinamates, sulfotriglycerides, amide soaps, alkyl oligoglucoside sulfates and alkyl(ether)phosphates. If the anionic surfactants contain polyglycol ether chains, they may have a conventional homolog distribution although they preferably have a narrow homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides and protein hydrolyzates (more particularly vegetable soya-based products). If the nonionic surfactants contain polyglycol ether chains, they may have a conventional homolog distribution although they preferably have a narrow homolog distribution.

Typical examples of cationic surfactants are quaternary ammonium compounds and esterquats, more particularly quaternized fatty acid trialkanolamine ester salts.

Typical examples of amphoteric or zwitterionic surfactants are alkyl betaines, alkyl amidobetaines, aminopropionates, aminoglycinates, imidazolinium betaines and sulfobetaines.

All the surfactants mentioned are known compounds. Information on their structure and production can be found in relevant synoptic works, cf. for example J. Falbe (ed.), (Surfactants in Consumer Products", Springer Verlag, Berlin, 1987, pages 54 to 124 or J. Falbe (ed.), "Katalysatoren, Tenside und Mineralöladditive", Thieme Verlag, Stuttgart, 1978, pages 123–217.

The detergent mixtures according to the invention may contain the additional surfactants mentioned above in quantities of 1 to 50% by weight and preferably in quantities of 5 to 25% by weight, based on the solids content of the mixtures.

COMMERCIAL APPLICATIONS

The detergent mixtures according to the invention are distinguished by particularly advantageous foaming power and by synergistically improved dermal compatibility—properties which are important in the development of a number of surface-active formulations.

Accordingly, the present invention also relates to surface-active formulations containing these detergent mixtures which are defined in more detail in the following:

Powder-form heavy-duty detergents containing 10 to 30% by weight, based on the detergent, of the detergent mixtures according to the invention and typical auxiliaries and additives.

Liquid heavy-duty detergents containing 10 to 70% by weight, based on the detergent, of the detergent mixtures according to the invention and typical auxiliaries and additives.

Liquid light-duty detergents containing 10 to 50% by weight, based on the detergent, of the detergent mixtures according to the invention and typical auxiliaries and additives.

Fabric softeners containing 10 to 50% by weight, based on the softener, of the detergent mixtures according to the invention and typical auxiliaries and additives.

Manual dishwashing detergents containing 10 to 50% by weight, based on the detergent, of the detergent mixtures according to the invention and typical auxiliaries and additives.

Rinse aids containing 10 to 50% by weight, based on the rinse aid, of the detergent mixtures according to the invention and typical auxiliaries and additives.

Liquid cleaners and disinfectants containing 10 to 30% by weight, based on the cleaner/disinfectant, of the detergent mixtures according to the invention and typical auxiliaries and additives.

Bar soaps of the combination bar type containing 1 to 2% by weight, based on the bar soap, of the detergent mixtures according to the invention and typical auxiliaries and additives.

Syndet soaps containing 1 to 2% by weight, based on the syndet soap, of the detergent mixtures according to the invention and typical auxiliaries and additives.

Hair shampoos containing 10 to 30% by weight, based on the shampoo, of the detergent mixtures according to the invention and typical auxiliaries and additives.

Hair rinses containing 10 to 30% by weight, based on the hair rinse, of the detergent mixtures according to the invention and typical auxiliaries and additives.

Hair colorants containing 10 to 30% by weight, based on the colorant, of the detergent mixtures according to the invention and typical auxiliaries and additives.

Hair wave sets containing 10 to 30% by weight, based on the wave set, of the detergent mixtures according to the invention and typical auxiliaries and additives.

Foam baths containing 10 to 30% by weight, based on the foam bath, of the detergent mixtures according to the invention and typical auxiliaries and additives.

Textile and fiber auxiliaries containing 1 to 30% by weight, based on the auxiliary, of the detergent mixtures according to the invention and typical auxiliaries and additives.

Leather oiling formulations containing 1 to 30% by weight, based on the oiling formulation, of the detergent mixtures according to the invention and typical auxiliaries and additives.

Flotation aids containing 1 to 30% by weight, based on the flotation aid, of the detergent mixtures according to the invention and typical auxiliaries and additives.

Auxiliaries for the dewatering of solids containing 1 to 30% by weight, based on the auxiliary, of the detergent mixtures according to the invention and typical auxiliaries and additives.

Auxiliaries and Additives

Laundry detergents, dishwashing detergents, cleaners and fabric softeners based on the detergent mixtures according to the invention may contain, for example, builders, salts, bleaching agents, bleach activators, optical brighteners, redeposition inhibitors, solubilizers and enzymes as further auxiliaries and additives in addition to the surfactants already mentioned.

Typical builders are sodium aluminium silicates (zeolites), phosphates, phosphonates, ethylenediamine tetraacetic acid, nitrilotriacetate, citric acid and/or polycarboxylates.

Suitable salts and extenders are, for example, sodium sulfate, sodium carbonate or sodium silicate (waterglass).

Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Hair shampoos, hair lotions or foam baths may contain emulsifiers, such as alkoxylated fatty alcohols or sorbitan esters for example, as further auxiliaries and additives in addition to the surfactants already mentioned.

Suitable superfatting agents are such substances as, for example, polyethoxylated lanolin derivatives, lecithin derivatives and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride.

Suitable biogenic agents are, for example, plant extracts and vitamin complexes.

Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, phenoxyethanol, formaldehyde solution, parabens, pentanediol or sorbic acid.

Suitable pearlescers are, for example, glycol distearic acid esters, such as ethylene glycol distearate, and fatty acid monoglycol esters.

The dyes used may be any of the substances suitable and licensed for cosmetic purposes, as listed for example in the publication entitled "Kosmetische Färbemittel" der Farbstoffkommission der Deutschen Forschungsgemeinschaft, published by Verlag Chemie, Weinheim, 1984, pages 81–106. These dyes are normally used in concentrations of 0.001 to 0.1 % by weight, based on the mixture as a whole.

The total content of auxiliaries and additives may be 1 to 50% by weight and is preferably 5 to 40% by weight, based on the particular formulation.

Finally, the present invention relates to the use of the detergent mixtures according to the invention for the production of liquid or solid surface-active formulations in which they may be present in quantities of 1 to 99% by weight and preferably 10 to 90% by weight, based on the solids content of the formulation.

EXAMPLES

I. Surfactants Used

A1) $C_{12/18}$ cocomonoglyceride sulfate sodium salt
B1) Coconut fatty acid isethionate sodium salt
B2) Coconut fatty acid taurate sodium salt
B3) Coconut fatty acid sarcosinate sodium salt II. Results of Performance Tests Foaming power was determined in accordance with DIN 53902, Part 2 (Ross Miles Test). 1% by weight surfactant solutions in water with a hardness of 16° d were used; the temperature was 20° C. Basic foam and foam volume after 5 mins. were determined.

The irritation potential was determined by OECD Method No. 404 and in accordance with EEC Directive 841449 EEC, Pt.B.4. The total irritation scores shown were formed from the irritation scores obtained after 24, 48 and 72 hours. The total irritation score for a 100% $C_{12/18}$ coconut fatty acid monoglyceride sulfate sodium salt determined in comparison test C1 was put at 100% and the total irritation scores obtained in the other tests were related to that score.

The results are set out in Table 1 (percentages as % by weight).

TABLE 1

Foaming Power and Irritation Potential

| Ex. | [A1] | B | [B] | Foam Height [ml] Immediately | After 5 Mins. | Total Irritation Score %-Rel |
|---|---|---|---|---|---|---|
| 1 | 50 | B1 | 50 | 550 | 420 | 65 |
| 2 | 70 | BI | 30 | 570 | 430 | 59 |
| 3 | 70 | B2 | 30 | 570 | 400 | 59 |
| 4 | 70 | B3 | 30 | 570 | 420 | 59 |
| C1 | 100 | — | — | 500 | 300 | 100 |
| C2 | 0 | B1 | 100 | 350 | 210 | 95 |
| C3 | 0 | B2 | 100 | 350 | 220 | 98 |
| C4 | 0 | B3 | 100 | 340 | 220 | 93 |

What is claimed is:

1. Surfactant mixtures providing improved dermal compatibility and foam stability, said surfactant mixtures comprising:

(a) monoglyceride(ether)sulfates, corresponding to formula (I):

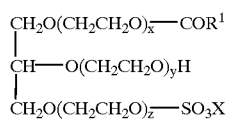

(I)

in which $R^1CO$ is a linear or branched acyl group containing 6 to 22 carbon atoms, x, y and z together represent numbers of 1 to 30 and X is an alkali metal or alkaline earth metal; and (b) fatty acid condensation products selected from the group consisting of (b1) fatty acid isethionates, (b2) fatty acid taurates and/or (b3) fatty acid sarcosinates.

2. Surfactant mixtures according to claim 1 present in a detergent composition.

3. Surfactant mixtures according to claim 2 wherein said detergent composition is a granular heavy-duty composition and said surfactant mixtures are present therein in an amount of 10% to 30% by weight, based on the weight of said detergent composition.

4. Surfactant mixtures according to claim 2 wherein said detergent composition is a liquid heavy-duty composition and said surfactant mixtures are present therein in an amount of 10% to 70% by weight, based on the weight of said detergent composition.

5. Surfactant mixtures according to claim 2 wherein said detergent composition is a liquid light-duty composition and said surfactant mixtures are present therein in an amount of 10% to 50% by weight, based on the weight of said detergent composition.

6. Surfactant mixtures according to claim 2 wherein said detergent composition is a manual dishwashing detergent composition and said surfactant mixtures are present therein in an amount of 10% to 50% by weight, based on the weight of said detergent composition.

7. Surfactant mixtures according to claim 1 present in a liquid cleaner/disinfectant composition in an amount of 10% to 30% by weight, based on the weight of said composition.

8. Surfactant mixtures according to claim 1 present in a rinse aid composition in an amount of 10% to 50% by weight, based on the weight of said composition.

9. Surfactant mixtures according to claim 1 present in a bar soap composition in an amount of 1% to 2% by weight, based on the weight of said composition.

10. Surfactant mixtures according to claim 1 present in a hair shampoo composition in an amount of 10% to 30% by weight, based on the weight of said composition.

11. Surfactant mixtures according to claim 1 present in a hair rinse composition in an amount of 10% to 30% by weight, based on the weight of said composition.

12. Surfactant mixtures according to claim 1 present in a hair coloring composition in an amount of 10% to 30% by weight, based on the weight of said composition.

13. Surfactant mixtures according to claim 1 present in a hair wave set composition in an amount of 10% to 30% by weight, based on the weight of said composition.

14. Surfactant mixtures according to claim 1 present in a bubble bath composition in an amount of 10% to 30% by weight, based on the weight of said composition.

15. Surfactant mixtures according to claim 1 present in a textile treating composition in an amount of 1% to 30% by weight, based on the weight of said composition.

16. Surfactant mixtures according to claim 1 present in a leather oiling composition in an amount of 1% to 30% by weight, based on the weight of said composition.

17. Surfactant mixtures according to claim 1 present in a flotation aid composition in an amount of 1% to 30% by weight, based on the weight of said composition.

18. Surfactant mixtures according to claim 1 present in a water treatment composition in an amount of 1% to 30% by weight, based on the weight of said composition.

* * * * *